Figure 1:
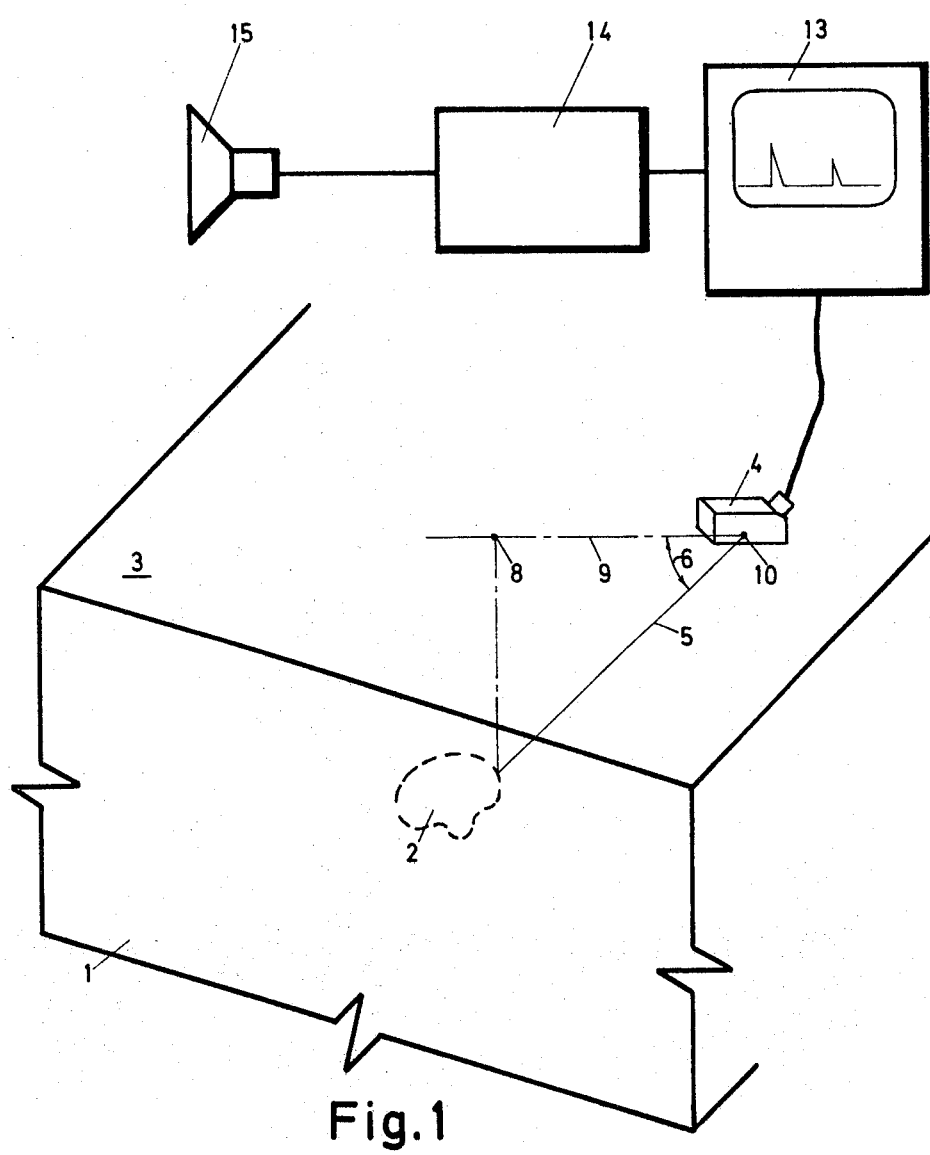

United States Patent [19]

Iversen et al.

[11] 4,088,030
[45] May 9, 1978

[54] APPARATUS FOR ULTRASONIC EXAMINATION

[75] Inventors: Sven Erik Iversen, Charlottenlund; Svend Aage Lund, Birkerod, both of Denmark

[73] Assignee: Akademiet for de Tekniske Videnskaber, Svejsecentralen, Glostrup, Denmark

[21] Appl. No.: 675,073

[22] Filed: Apr. 8, 1976

[30] Foreign Application Priority Data
Apr. 15, 1975 Denmark ............... 1615/75

[51] Int. Cl.² ........................... G01N 29/04
[52] U.S. Cl. ........................... 73/629
[58] Field of Search ........... 73/67.7, 67.5 R, 67.8 R, 73/67.9; 340/261

[56] References Cited

U.S. PATENT DOCUMENTS

| 3,585,851 | 6/1971 | Walther ............... 73/67.9 |
| 3,672,210 | 6/1972 | Cressman et al. ........ 73/67.9 |
| 3,813,926 | 6/1974 | Stubbeman ............. 73/67.7 |
| 3,962,909 | 6/1976 | Lund .................. 73/67.9 |

Primary Examiner—Richard C. Queisser
Assistant Examiner—Stephen A. Kreitman
Attorney, Agent, or Firm—Schuyler, Birch, Swindler, McKie & Beckett

[57] ABSTRACT

In an apparatus for locating inhomogeneities in otherwise homogeneous bodies by the ultrasonic pulse-echo method an angle probe is used in connection with an acoustic signal emitter, adapted to produce an audible signal, a characteristic of which, e.g. the intensity, varies in a continuous manner with the amplitude of the reflected ultrasonic pulses.

2 Claims, 3 Drawing Figures

APPARATUS FOR ULTRASONIC EXAMINATION

The invention relates to an apparatus for locating internal inhomogeneities in otherwise homogeneous objects, which have a substantially plane or slightly curved surface, by ultrasonic examination according to the pulse-echo method by the use of an ultrasonic apparatus comprising at least one probe which can be guided freely in a two-dimensional movement across the surface of the object and at the same time be turned around an axis which is at right angles to the plane of the surface.

In ultrasonic examinations it is customary to use an ultrasonic apparatus comprising an incorporated oscilloscope, on the screen of which indications are displayed of the reflected ultrasonic pulses which are received in the form of echoes from internal inhomogeneities in the objects examined. These indications usually consist of vertical lines, the heights of which are proportional to the amplitudes of the reflected ultrasonic pulses, and the horizontal distances of which from a fixed zero point are proportional to the total forward and return transit times of the corresponding ultrasonic pulses in the object, the so-called A-display or A-scan.

During a conventional manual ultrasonic examination, the operator guides the probe in a two-dimensional movement across the surface of the object and at the same time turns it in various directions to hunt for echoes from internal inhomogeneities, if any. When an echo is displayed on the screen of the oscilloscope, the operator then has to examine the flaw found more closely and locate it. Primarily, this is effected by the probe being displayed and turned until the echo indication displayed on the screen has reached its maximum height. Then the echo height is recorded, which gives information as regards the nature and size of the flaw, as well as the echo distance which forms the basis of the accurate calculation of the position of the flaw in the object.

In the case of an extensive examination this method is exceedingly tiring and requires incessant concentration since the operator all the time has to divide his attention between following the movement of the probe in relation to the object and at the same time watching the constantly changing display on the screen of the ultrasonic apparatus. In addition, this continuous division of the operator's attention involves a considerable risk that flaws are either overlooked or are not located with the necessary precision.

In order to remedy these drawbacks it has, inter alia, been attempted to develop mechanized ultrasonic examination methods comprising automatic guiding of the probe and automatic printing or drawing of the echo pulses recorded. Such systems certainly function satisfactorily, but, for one thing, they are exceedingly expensive and, secondly, they can substantially be used only under laboratory or workshop conditions and for the examination of completely identical objects. Under conditions on construction sites and in the examination of widely different objects, which is by far the largest field of ultrasonic examinations, the mechanized systems normally cannot be applied.

In the specifications of U.S. Pat. No. 3,939,697 with patent of addition No. 3,962,909 it has furthermore been suggested to provide a visual indication in the place of examination proper by using a row of punctiform light-emitting diodes and by letting light emission from a single one or a number of these light-emitting diodes represent the amplitude of a reflected ultrasonic pulse. Certainly, such systems also function satisfactorily, even under conditions on construction sites, but it has likewise turned out that they are too expensive for being generally used at conventional ultrasonic examination in practice, since the manufacturing costs for merely the light-emitting diode systems and the associated electronic control systems have proved to be so high that they are of the same order of magnitude as for a complete conventional ultrasonic equipment.

Finally it has been suggested, inter alia in the specifications of the U.S. Pat. Nos. 2,836,059 and 3,813,926, to provide ultrasonic apparatuses with an acoustic or visual alarm device which warns the operator when echo pulses are received that are above or below predetermined limit values. Such devices do not, however, relieve the operator of the above-mentioned exacting and tiring work connected with the exact determination of the position, nature and size of the flaws found.

It is the object of the present invention to provide an apparatus for ultrasonic examination which likewise is universally applicable and makes it unneccessary for the operator to watch the echo indications on the oscilloscope screen of the apparatus constantly, but which makes possible a more reliable and accurate examination and which can be manufactured at a fraction of the cost connected with the systems of the corresponding types so far known.

According to the invention this is achieved by an angle probe being used which transmits and receives short ultrasonic pulses in directions forming a predetermined angle, different from 90°, with the surface of the object, and by the ultrasonic apparatus being via control circuit arrangements connected to an acoustic signal emitter and being so arranged that on the reception of a reflected ultrasonic pulse an audible sound signal is produced, the intensity, frequency and/or duration of which varies in a continuous manner with the amplitude of the reflected ultrasonic pulse.

By this means is achieved that the operator can concentrate his full attention on viewing the place of examination proper without constantly having to watch the varying display on the oscilloscope screen of the ultrasonic apparatus. The result of this is that the examination work becomes far less tiring and consequently considerably more reliable than is the case with the prior art apparatuses using oscilloscopes. Since furthermore the human ear is particularly sensitive to even very small variations in an audible sound signal, particularly variations in the frequency of the said signal, the examination can at the same time be made more reliable with regard to ascertaining all occuring flaw echoes, and more precise than has so far been the case as regards the localization of the position in which an internal flaw gives the maximum reflection of the ultrasonic pulses. Finally, an acoustic signal emitter with its associated control circuits can be manufactured at a relative low cost, and consequently the apparatus becomes essentially less expensive than the apparatuses of the corresponding type known so far.

A particularly expedient embodiment of the invented apparatus is characterized in that in addition there is in fixed connection with the angle probe mounted a holder in which an indicating member is placed which points towards the surface of the object and which is movable relative to the holder in such a way that is can be displaced along a straight line which is parallel to the projection of the sound path on the surface of the object, and in that the indicating member in a way known per se via a position transducer, switching means and control circuit arrangements is connected to the ultrasonic apparatus and the acoustic signal emitter in such a way that, with the switching means in a given position, an audible sound signal, the intensity, frequency and/or duration of which varies in a continuous manner with the amplitude of the reflected ultrasonic pulse is produced when and only when the indicating member is located at a distance from the sound emitting point of the probe which has a given ratio to the total forward and return transit time of a reflected ultrasonic pulse in the object.

The result of this is an additionally increased facilitation and precision in the localization of the exact position in which an internal flaw gives the maximum reflection of the ultrasonic pulses. Since the total forward and return transit time for the ultrasonic pulses is directly proportional to the distance from the sound emitting point of the probe to the internal point of reflection, the operator can, by a suitably chosen ratio and with the switching means in the said position, without having to read the display on the screen of the oscilloscope and without performing any geometrical calculations by only setting the indicating member according to the sound signal produced, directly on the surface read and mark off the point representing the projection on the surface of the object of the internal reflection point in question.

Finally, an embodiment of the apparatus according to the invention is characterized in that in addition to the angle probe and the holder with indicating member and position transducer mounted on the probe, as well as an acoustic signal emitter and switching means, it consists only of a conventional transmitting circuit arrangement and receiving circuit arrangement for electric pulses to and from the probe as well as two control circuit arrangements for actuating the acoustic signal emitter, which four circuit arrangements may expediently be built together so as to form a single integral and preferably battery-powered unit.

The result of this is a portable pocket-size miniature ultrasonic apparatus which the operator can easily carry on his person, and which can be used under widely different conditions and even in places where it would be difficult to use a normal ultrasonic apparatus. In addition, the apparatus will be considerably less expensive than the prior art apparatuses which require the use of an oscilloscope with the associated expensive control circuits.

Figure 2:
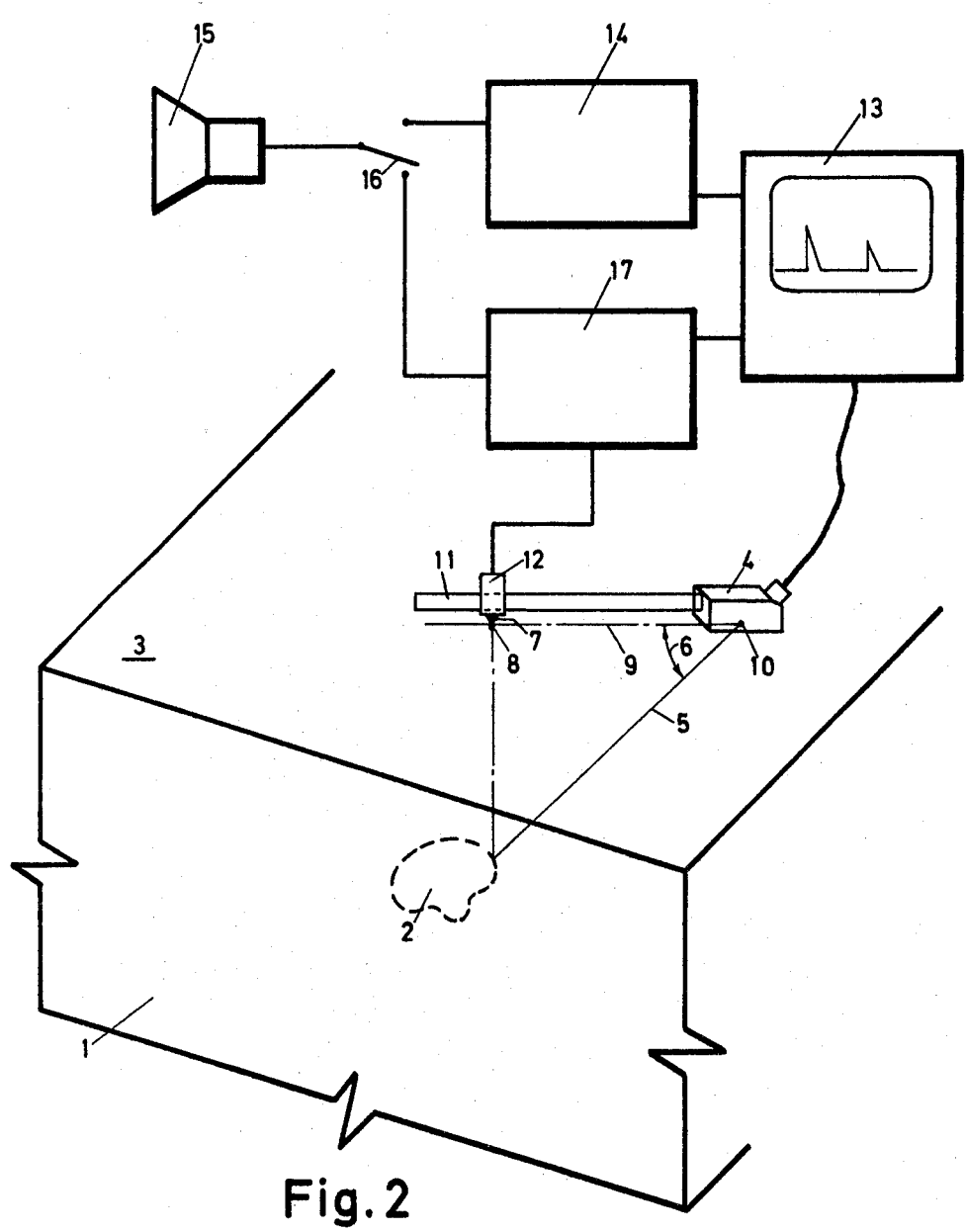
Figure 3:
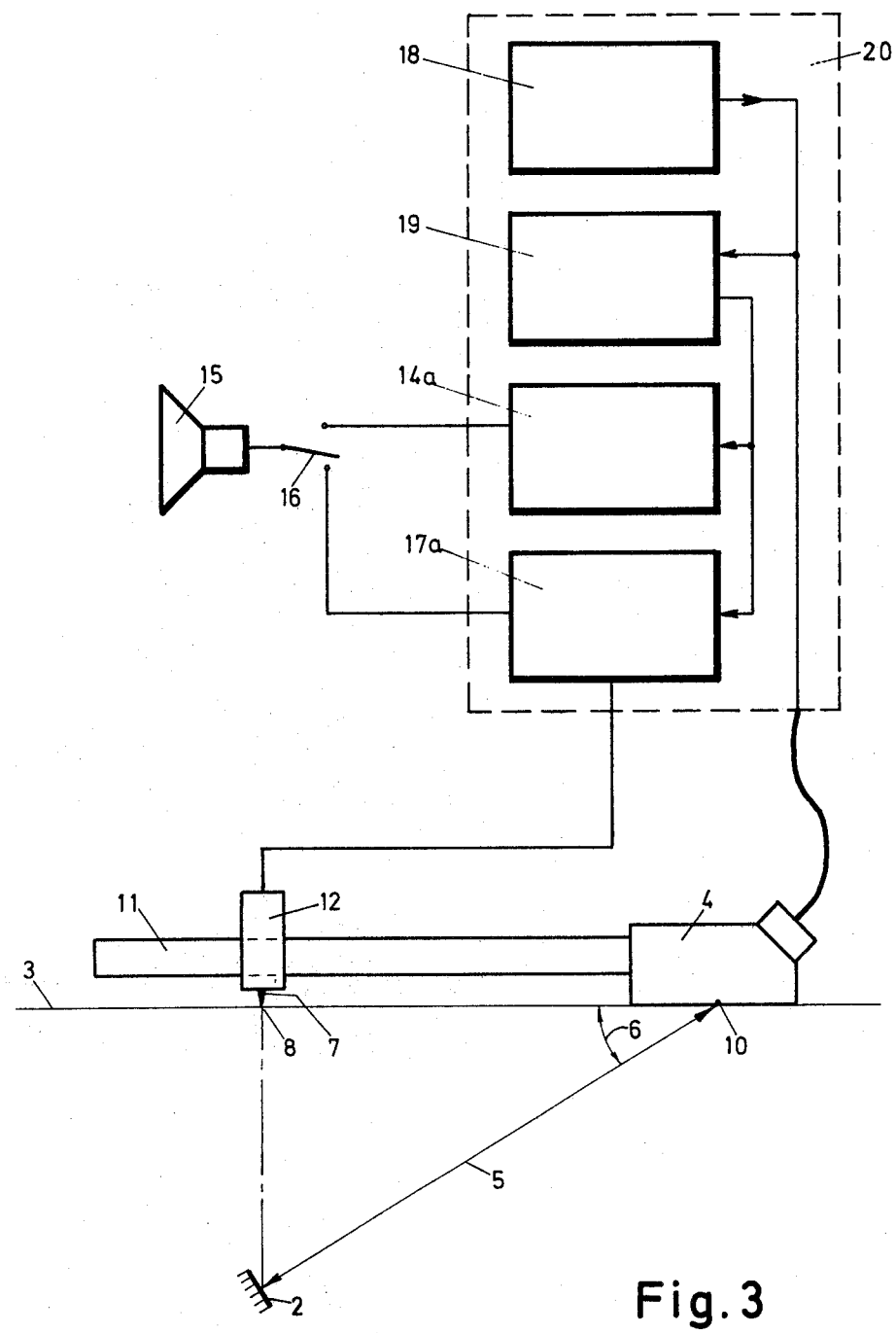

Below, the invention is explained in greater detail with reference to the schematical drawing in which FIG. 1 schematically and partly in perspective shows an embodiment of the apparatus according to the invention and the principle of its application in an ultrasonic examination, FIG. 2 schematically and partly in perspective shows another embodiment of the apparatus according to the invention and the principle of its application in an ultrasonic examination and FIG. 3 schematically shows an embodiment of a portable pocket-size miniature ultrasonic apparatus with ultrasonic probe, holder and indicating member viewed in side elevation.

FIG. 1 shows an object 1 having an internal inhomogeneity 2 acting as a reflection point for ultrasonic pulses. These pulses are produced by means of a conventional ultrasonic apparatus 13, comprising an oscilloscope, via an ultrasonic probe 4 which is placed on the plane or substantially plane surface 3 of the object and is arranged for transmitting and receiving pulses in a direction 5 forming an angle 6, different from 90°, with the surface of the object. The echo signals received by the probe are returned to the ultrasonic apparatus 13 and displayed on the screen of the oscilloscope together with the ultrasonic pulse transmitted. The electric signals corresponding to the echo pulses received are also supplied to an electronic control circuit arrangement 14 which controls an acoustic signal emitter 15 in such a way that at the reception of a reflected ultrasonic pulse an audible sound signal is produced, the intensity, frequency and/or duration of which varies in a continuous manner with the amplitude, that is to say the intensity, of the reflected ultrasonic pulse.

The apparatus is normally used in the way that an operator guides the probe 4 in a two-dimensional movement across the surface 3 of the object and at the same time turns it in different directions to hunt for echoes from internal inhomogeneities, if any. When an audible sound signal is emitted from the signal emitter 15, the operator then has to examine the flaw found in greater detail and locate it. This is effected by the probe 4 being displaced and turned until the audible sound signal indicates that the amplitude of the reflected ultrasonic pulses has reached its highest possible value, that is to say until the flaw is centered accurately relative to the conical sound beam emitted from the probe. On the basis of the nature of the sound signal the operator can estimate the nature and size of the flaw, and on the basis of the knowledge of the angle 6, the direction of the probe on the surface of the object, the velocity of the sound in the material of the object as well as the deflection velocity and the horizontal spacing between the starting pulse and the flaw echo on the display of the ultrasonic apparatus the operator can next calculate and record the exact position of the flaw 2 in the object 1.

As acoustic signal emitter it will frequently be expedient to use headphones or earphones which the operator can carry during the performance of the examination.

The dependence of the sound signal on the amplitude of the reflected ultrasonic pulses may according to the circumstances be arranged in different ways. The sound intensity proper may for instance be made directly proportional to the echo amplitude, or the sound signal may be divided into short sound signals, the duration of which is made proportional to the echo amplitude. It will be particularly expedient as sound signal to use a tone signal, the frequency of which varies proportionally to the echo amplitude, since the human ear seems to be particularly sensitive to even very small variations in the pitch of a sound.

FIG. 2 shows another embodiment of the apparatus invented. The apparatus is arranged and functions in the same way as that described above in connection with FIG. 1, but in fixed connection with the probe 4 a holder 11 has been added in which an indicating member 7 in the form of a pointer or a similar member has been mounted which points towards the surface 3 of the object and is movable in such a way relative to the holder 11 that it can be displaced along a straight line parallel to the projection 9 of the sound path 5 on the surface 3 of the object.

When the indicating member 7 is displaced along the holder 11, its distance from the sound emitting point 10 of the probe is constantly being sensed by a conventional position transducer 12, for instance in the form of the slide on a rheostat.

The position transducer 12 is via an electronic control circuit arrangement 17 connected to the ultrasonic apparatus 13 as well as via switching means 16 to the acoustic signal emitter 15 in such a way known per se that with the switch 16 in the bottom position in FIG. 2 an audible sound signal is produced, the intensity, frequency and/or duration of which depends on the amplitude of the reflected ultrasonic pulse, when and only when the indicating member 7 is located at a distance from the sound emitting point 10 of the probe which has a given ratio to the total forward and return transit time in the object 1 of a reflected sound pulse.

The transit time for an ultrasonic pulse is proportional to the distance from the sound emission point 10 to the point of reflection 2, and when the factor of proportionality between the transit time and the distance from the sound emission point 10 to the indicating member 7 is in a way known per se adapted to the angle 6 and to the sound velocity in the material of the object the expedient result can be achieved that the indicating member 7, when set in such a way that the sound signal from the signal emitter 15 indicates the maximum amplitude for the reflected ultrasonic pulses, will point exactly towards the point 8 which represents the projection of the reflection point on the surface 3 of the object.

The apparatus is normally used in exactly the same way as explained above in connection with FIG. 1. Thus, when the probe 4 with the switch 16 in its top position in FIG. 2 is by means of the sound signal from the acoustic signal emitter 15 placed and centered accurately relative to the reflection point 2, the operator switches the switch 16 from the control circuit arrangement 14 to the control circuit arrangement 17 and subsequently reciprocated the indicating member 7 along the holder 11 and hereby hunts for the position in which the sound signal from the signal emitter 15 indicates the maximum amplitude for the reflected ultrasonic pulses. When this has been achieved, the operator can directly on the surface of the object read and mark off the point 8 which represents the projection on the surface of the object of the same reflection point without it being necessary for the operator to perform geometrical calcculations. of any kind.

It will frequently be expedient to use the same type of sound signal, first at the centering of the probe 4 and later when the indicating member 7 is placed relative to the probe so that at the final determination of the position the operator can directly recognize the same sound signal as a moment earlier was used for centering the probe. It may, however, also be expedient to use two different types of sound signals to avoid that the operator by a mistake gets the two setting operations mixed up.

I may also be expedient to use the apparatus according to the present invention in combination with one of the apparatuses for recording projection images of internal inhomogeneities which are described in the specifications of U.S. Pat. Nos. 3,939,697 and 3,962,909 so that simultaneously with the precision adjustment, controlled by sound signals, of the indicating member 7 there will occur a recording of corresponding precise projection images of the internal inhomogeneities in the object found by the ultrasonic examination.

The apparatus invented may expediently in a way known per se be arranged in such a way that audible sound signals are produced only when reflected ultrasonic pulses are received, the amplitudes of which exceed a predetermined value. By this means, the ultrasonic examination of a given object may be concentrated solely on finding flaws of such a size that they are regarded as essential in the particular case.

FIG. 3 shows an ultrasonic apparatus according to the present invention which is designed as a pocket-size miniature apparatus. In addition to the ultrasonic probe 4 and holder 11 with the indicating member 7 and the position transducer 12 mounted on the probe as well as the acoustic sound emitter 15 and the switching means 16 the apparatus comprises only a transmitter 18 for ultrasonic pulses, a receiver 14 for the echo pulses as well as the two electronic control circuit arrangements 14a and 17a for actuating the acoustic signal emitter 15. The components 18, 19 14a and 17a are expediently built together so as to form an integral apparatus 20 which may be battery-powered. The apparatus 20 can easily be made so small that it can conveniently be carried in a pocket, and since the apparatus can be independent of outer current supply it may be used under virtually all conditions. In addition, it is possible to manufacture the apparatus at a considerably lower cost than the known ultrasonic apparatuses which comprise an oscilloscope with the associated expensive control circuits. This is made possible by information regarding the maximum amplitudes for the reflected ultrasonic pulses as well as information regarding the transit time for the ultrasonic pulses, which in the known apparatuses are obtained from the oscilloscope, being here obtained directly by means of the audible sound signals from the acoustic signal emitter 15. If it be desired, the apparatus 20 and possibly also the switch 16 and the signal emitter 15 can be built together with the ultrasonic probe 4, so that the total examination equipment consists of a single unit. Also in the embodiment shown in FIG. 1 the miniaturizing principle illustrated in FIG. 3 can be used.

What is claimed is:

1. An apparatus for locating internal inhomogeneities in an otherwise homogeneous object, having a substantially plane or slightly curved surface, utilizing the pulse-echo method of ultrasonic examination comprising:

a probe which can be guided freely in two-dimensional movement across the surface of the object and can be freely rotated about an axis which is at a right angle to the plane of the surface, wherein the probe transmits ultrasonic pulses and receives reflected ultrasonic pulses in a path forming a predetermined angle, other than 90°, with the surface;

an ultrasonic circuit means coupled to the probe for producing and processing the ultrasonic pulses which are transmitted and received by the probe;

an acoustic emitter means for producing an audible sound signal;

a first control circuit means coupled to the ultrasonic circuit means and the acoustic emitter means for converting the received reflected ultrasonic pulses to a signal which continuously varies in intensity, frequency, or duration so that the acoustic emitter means produces an audible sound signal which varies in a continuous manner with the amplitude of the received reflected ultrasonic pulse;

an elongated holder affixed to the probe;

a positioned transducer slidably mounted on and movable relative to the holder in a direction along a straight line parallel to the projection of the pulse path on the surface;

an indicating means mounted on the positioned transducer for indicating the point on the surface which represents the projection of the inhomogeneity on the surface;

a two-position switch means for connecting the acoustic emitter means to said first control circuit means when said switch is in a first position; and a second control circuit means coupled to said acoustic emitter means when said switch means is in a second position, said second circuit means being coupled to said ultrasonic circuit means and said positioned transducer for converting the received reflected ultrasonic pulses to a signal which continuously varies in intensity, frequency, or duration so that the acoustic emitter means produces an audible sound signal which varies in a continuous manner with the amplitude of the received reflected ultrasonic pulse when and only when said indicating means is located at a distance from said probe which has a given ratio to a total forward and return transit time of said ultrasonic pulses and reflected ultrasonic pulses, respectively.

2. The apparatus of claim 1 wherein said ultrasonic circuit means, said first control circuit means, and said second control circuit means are built together so as to form a single integral unit.

* * * * *